United States Patent [19]

Shoemaker

[11] Patent Number: 4,835,260

[45] Date of Patent: May 30, 1989

[54] ERYTHROPOIETIN COMPOSITION

[75] Inventor: Charles B. Shoemaker, Belmont, Mass.

[73] Assignee: Genetics Institute, Inc., Cambridge, Mass.

[21] Appl. No.: 28,282

[22] Filed: Mar. 20, 1987

[51] Int. Cl.$^4$ ..................... C07K 13/00; C12N 15/00; C12N 5/02; C12P 21/02

[52] U.S. Cl. .................................. 530/397; 530/350; 530/380; 530/399; 530/395; 530/829; 530/830; 435/68; 435/172.3; 435/240.2; 514/8; 514/21; 514/814; 935/13; 935/19; 935/70; 536/27; 536/28; 536/29

[58] Field of Search .................... 435/172.3, 68, 240.2; 514/8, 814, 2; 530/380, 397, 350, 399, 395; 935/13; 536/28, 27, 29

[56] References Cited

U.S. PATENT DOCUMENTS 4,652,639 3/1987 Stabinsky .................... 435/172.3
4,752,585 6/1988 Koths et al. .

FOREIGN PATENT DOCUMENTS

85/03079 7/1985 PCT Int'l Appl. .............. 935/172.3
2171303 8/1986 United Kingdom ................. 514/814

OTHER PUBLICATIONS

Zoller et al, Nuc. Acid. Res., 10(20), 6487 (1982).
Chem. Abs. 100:28516d (for PCT Int. Appl. WO86/03520, 19 Jun. 1986, Fritzch et al; Genetics Inst.).
Chem. Abs. 104:466969 (for PCT Int. Appl. WO8502610, 20 Jun. 1985, Lin (Kirin Amgen)).
Lin et al, Proc. Nat. Acad. Sci USA, 82, 7580-7584 (1985).
McDonald et al, Mol. Cell. Biol.; 6(3), 842-848 (1986).
Lee Huang, Proc. Nat. Acad. Sci., 81, 2708-12 (1984).
Powell et al, Proc. Nat. Acad. Sci., 83, 6465-69 (1986).
Jacobs et al, Nature, 313, 806-10 (1985).
Chem. Ab. 104:15689w (for Egrie et al, Prog. Clin. Biol. Res., 191, 339-50 (1985).
Chem Ab. 106:182619w (for Osamu et al, Fr. Demande, FR 2576 792, 8 Aug. 1986).
Chem. Ab. 106:169227x (for Davis et al, Biochemistry, 26(9), 2633-38 (1987).
Shoemaker and Mitsock, Mol Cell Biol., 6(3), 849-858 (1986).

Primary Examiner—Margaret Moskowitz
Assistant Examiner—Jeff P. Kushan
Attorney, Agent, or Firm—Bruce M. Eisen; Ellen J. Kapinos; David L. Berstein

[57] ABSTRACT

A new improved glycoprotein having erythropoietin-type activity is disclosed. The substrate is characterized by amino acid sequence substantially identical to the amino acid sequence of native human erythropoietin wherein the methionine-54 is replaced with leucine. DNA encoding for the EPO-substance and expression vectors incorporating the same are disclosed. Therapeutic compositions and methods for treatment of anemic conditions are described.

4 Claims, No Drawings

ERYTHROPOIETIN COMPOSITION

This invention relates to a novel substance having erythropoietin-type activity. More particuolarly, it relates to the production of a erythropoietin-type substances prepared using recombinant DNA techniques, and the therapeutic use of these substances for treatment of anemic conditions.

It is well known that erythropoietin (hereafter referred to as EPO) is a glycoprotein hormone which maintains the number of circulating erythrocytes in the blood at a level necessary for optimal delivery of oxygen to the body tissues. This hormone is therefore important for the diagnosis and treatment of blood disorders characterized by low or otherwise defective red blood cell production. For instance. it has been shown that EPO can successfully treat various forms of anemia, particularly chronic renal failure wherein diseased tissues fail to sustain production of EPO.

EPO has been characterized and is known to be expressed as a 165 amino acid sequence. The amino acid sequence of EPO is disclosed in Genetics Institute PCT publication No. W086/03520, for example in Table 2. See also Jacobs et al. *Nature* 313 No. 6005, pp. 806–810 (1985).

The production of EPO using recombinant DNA techniques has been described by Jacobs et al.*Nature* 313 No. 6005, pp. 806–810 (1985), in Genetics Institute PCT publication No. WO 86/03520 (the disclosure of which is incorporated herein by reference), and in Kirin-Amgen PCT Publication No. WO 85/02610. Genetics Institute PCT publication No. WO 86/03520 describes the cloning of the EPO gene and cDNA, suitable vectors for the expression thereof, suitable hosts, purification schemes and related processes. The cloning of the human EPO gene and the expression of an EPO cDNA clone provides a major source of biologically active EPO.

The improved EPO compositions of the ivention are characterized by an amino acid sequence substantially identical to native EPO wherein the methionine residue at position 54 is replaced with a different naturally ocurring amino acid. The amino acid sequence is substantially identical to native EPO having at least 162 of the same amino acids in the same position. In a preferred embodiment the aforesaid position 54 contains leucine instead of methionine. In other preferred embodiments the methionine may be replaced with other naturally occurring amino acids having aliphatic hydrocarbon groups including isoleucine, valine, or alanine. In other embodiments, the EPO composition is further characterized by an amino acid sequence which, in addition to the substitution of methionine, also includes a substitution at asparagine residue 38 as described in copending application Ser. No. 028,280 filed Mar. 20, 1987. It is preferred that position 38 contains glutamine instead of asparagine. In a preferred embodiment position 54 contains leucine and position 38 contains glutamine. The invention also includes DNA encoding this protein, as well as therapeutic compositions and methods for administering the same.

The EPO compositions of this invention surprisingly retain the desirable biological activities of native EPO. It is further contemplated that the EPO substances produced according to the invention posses improved properties over EPO substances which have the exact amino acid sequence of native human EPO. The compositions are thought to have increased stability relative to natvie EPO. It also appears that there is no reduction in yield of expression though such a reduction has been demonstrated with other changes. These and other desirable properties resulting from replacement of the methionine - 54 with leucine are especailly surprising since EPO is expected to be exquisitely sensitive to change. For instance, it has been shown that the amino acid sequence of EPO has remained highly conserved during evolution. Shoemaker and Mitzock *Mol. Cell. Biol.* 6:849–858 (1986 ), found that mature EPO from human is 80% conserved when compared to the amino acid sequence from mouse. The methionine residue is within a stretch of 20 amino acids that are 100% conserved between the two species. Therefore, it would be expected that the EPO molecule would be sensitive to even minor amino acid changes. In particular, it would be expected that a change in methionine, given its location in an area of 100% conservation, would deliteriously affect the molecule and its activity. It has also been demonstrated that the conversion of sulfur-containing cysteine to serine results in markedly diminished secretion of EPO and reduced specific activity. However, the EPO composition of the invention retains the activity of native human EPO.

The EPO composition of the invention is also contemplated to have no detrimental immunogenic properties relative to more drastically modified analogues. This is highly desirable given the chronic administration of EPO in the treatment of anemia.

It is further contemplated that substitution of the sulfur-containing methionine with leucine renders the EPO substance less susceptible to oxidation. These oxidization conditions can ocuur during purfication, formulation or storage of the recombinant protein prior to its administration as a therapeutic agent. Reduction in susceptibility to oxidation is therefore quite significant and highly desirable. The EPO substance of the invention is rendered less susceptible to oxidation without sacrificing the desirable biological and immunological properties of the naturally occurring human EPO.

Substitution of methionine-54 with a different amino acid results in the further advantage of minimizing misincorporation of norleucine. Norleucine is a synthetic amino acid analogue which is known to incorporate into proteins at positions normally occupied by methionine. It has also ben postulated that norleucine is produced as a cellular metabolite which can build up and therefore potentially be misincorporated into a methionine position.

The EPO protein substances of the invention are produced by culturing mammalian cells transformed with the DNA sequence encoding these proteins. The DNAs are produced using site-specific mutagenesis of DNA encoding human EPO. As mentioned above, DNA sequences encoding human EPO are known in the art and have been cloned and characterized. The codon for the methionine residue at position 54 in the human EPO amino acid sequence is altered to create a leucine codon by conventional site-directed mutagenesis. Such methods of mutagenesis are well known to those skilled in the art and include for instance the M13 system of Zoller and Smith, *Nucleic Acids Res.* 10:6487–6500 (1982); *Methods Enzymat* 100:468–500 (1983); and *DNA* 3:479–488 (1984), using single stranded DNA and the method of Moringa et al., *Bio/technology*, 636–639 (July 1984), using heteroduplexed DNA. The altered coding DNA is then expressed by conventional means on a selectted host cell system which yields the desired EPO which is then recovered and purified.

The expression vectors in accordance with the invention may be synthesized by techniques well known to those skilled in the art. The components of the vectors such as the bacterial replicons, selection genes, enhancers, promoters, and the like may be obtained from natural sources or sythesized by known proceduresl. See Kaufman et al., *J. Mol Biol.*, 159:51–521(1982); Kaufman, *Proc Natl. Acad. Sci.* 82:689–693 (1985).

Established cell lines, including transformed cell lines, are suitable as hosts. Normal diplois cells, cell strains derived from *in vitro* culture of primary tissue, as well as primary explants (including relatively undifferentiated cells such as hematopoetic stem cells) are also suitable. Candidate cells need not be genotypically deficient in the selection gene so long as the selection gene is dominatly acting. Expression of the DNA may be carried out in mammalian, yeast, fungel, bacterial, or insect host cell systems. Established mammalian cell lines are currently the preferred host cells. In particular, CHO (Chinese hamster ovary) cells are presently preferred for stable integration of the vector DNA into chromosomal DNA, and for subsequent amplification of the intergrated vector DNA, both ny conventional methods. CHO cells transformed with EPO cDNA encoding leucine at position 54 were deposited with the American Type Culture Collection (ATCC) 12301 Parklawn Drive, Rockville, MD. on Dec. 21, 1988 under accession number CRL9933. Alternatively, the vector DNA may include all or part of the bovine papilloma virus genome (Lusky et al., *Cell*, 36:391–401 (1984)) and be carried in cell lines such as C127 mouse cells as a stable episomal element. Other usable mammalian cell lines include but are not limited to, HeLa, COS-1 monkey cells, mouse L-929 cells, 3T3 lines derived from Swiss, Balb-c or NIH mice, BHK or HaK hamster cell lined and the like.

Stable transformanta are then screened for expression of the product by standard immunological or enxymnatic assays. The presence of the DNA encoding the varient proteins may be detected by standard procedures such as Southern blotting. Transient expression of the DNA encoding the variants during the several days after introduction of the expression vector DNA into suitable host cells such as COS-1 monkey cells is measured without selection by activity or immunologic assay of the protiens in the culture medium.

The compounds expressed in the host cells may then be recovered, purified, and/or characterized with respect to physicochemical, biochemical and/or clinical parameters, all by known methods. The EPO substance of the invention may be recovered and/or purified by immunoaffinity chromatography using antibodies to human EPO. Reference is made to Genetic Institute PCT publication WO86/03520 for further description of suitable vectors, host cells and techniques. The invention will be further understood from the following non-limiting example:

EXAMPLE

Preparation of the cDNA encoding the EPO composition of the present invention is carried out by the substitution of methionine-54 with leucine using conventional site-directed mutagenesis of a DNA encoding human EPO in accordance with the methods of Zoller and Smith e.g. DNA 3:479–488 (1984) and therefore recitation of the detailed procedures will not to repeated herein. The Zoller and Smith methods involve a simple and efficient procedure for oligonucleotide-directed mutagenesis using M13-derived vectors. In general, an oligonucleotide consisting of the mutant sequence is hybridized to its complementary sequence in a clone of wild-type DNA to form a mutant wile-type heteroduplex. A double-stranded heteroduplex is formed and the mutant clones are distinguished from the wild-type by screening with a mutagenic oligonucleotide probe. The cDNA encoding human EPO is inserted into the M13 vector Mutagenesis at Met-54 is effected using the following oligonucleotide to convert the methionine codon to a leucine condon:

5'CTGGAAGAGGTTGGAGGTCG 3'

As those skilled in the art will appreciate, such an oligonucleotide can be readily constructed for use in replacing an amino acid with a different amino acid at a desired site by substituting the codon for the desired replacement amino acid in the oligonucleotide. The M13 vector is then used to transform E. coli JM101 cells. The plaques are screened for mutants by filter hybridiziation using the following mutagneic oligonucleotide as a probe in accordance with the methods of Zoller & Smith:

5'GAGGTTGGAGG 3'

The mutagenized cDNA is excised from the M13 vector and ligated into the expression vector pRK1-4 which has been deposited with the American Type Culture collection, Rockville, MD., where it is available under Asseccion Number ATCC 39940.

The specific activity of the expressed EPO is measured and compared with the specific activity of wild type EPO. The purified expression vector DNA containing the mutagenized cDNA was transfected into COS1 cells by the DEAE-dextran method as described in Sompayrac and Danna, *Proc. Natl. Acad. Sci. USA* 78:7575–7578. The medium was replaced after 2 days and EPO containing conditioned media was harvested 24 hours later. A second transfection was performed with purified expression vector DNA containing wild-type EPO cDNA that was performed and tested by the same procedures. *In vitro* activity of the EPO composition was assayed by the Krystal method *Exp. Hematol.* 11:649 (1983). This assay measures the stimulation of proliferation within a population of isolated spleen cells enriched for erythrocyte precursors. Phenylhydrazine is given by injection to mice creating a drug induced anemia that results in the accumulation of erythroid precursor cells in the spleen. The spleen is removed and the population of cells, enriched for erythroid progenitors, is isolated and cultured. These cells are partilcularly responsive to proliferation upon addition of EPO. Thus $^3$H-thymidine incorporation into these cells is increased well above background by culturing in the presence of EPO. Utilizing an EPO standard, a linear dose/response range is established. Unknown samples can be accurately assayed for EPO when they are diluted such that the $^3$H incorporation is within the linear response range of the standard curve.

As as method for determination of recombinant EPO protein concentration, a radioimmunoassay for EPO was conducted similar in design to procedures widely used for other antigens. the assay measures the ability of a sample to compete with radiolabled EPO for binding to antiserum that is specific for EPO. The ability to compete is related to the amount of EPO in the sample. This relationship is linear for a defined range of EPO. Calibrated standards are used to establish this linear range. The unknown sample is then diluted to an extent such that the competition for radiolabeled EPO is within the linear range of the assay. Based on this value, the EPO protein concentration can be calculated.

The specific activity of the mutant (met 54 to leu) EPO produced by COS-1 cells as measured in two separate assays was 853 u/ug and 914 u/ug, as compared to 939 u/ug and 1155 u/ug for the wild type EPO from COS-1 cells.

The invention also encompasses therapeutic compositions for the treatment of anemic conditions such as chronic renal failure. The composition consist of a therapeutically effective amount of the EPO protein of the invention in admixture with a pharmaceutically acceptable carrier, diluant, or adjuvant. The composition can be used in the same manner formulation, modes for administration and dosage required as that described for human EPO. The invention also includes a method for treatment of anemic conditions which comprises administering an effective amount of the EPO substance. The exact dosage and method of adminstration will be determined by the attending physician depending on potency and pharmacokinetic profile of the EPO substance as well as on various factors which modify the actions of drugs such as body weight, sex, diet, time of administation, reaction sensitivities and severity of the particulat case.

Further useful advantages of the EPO substance of the invention have been recognized. For instance, by replacement of the only methionine residue in the amino acid sequence of human EPO with another amino acid, the EPO molecule provided will not be susceptible to cyanogen bromide which is known to cleave methionine at the C-terminus. The EPO of this invention may therefore be produced as a fusion product by adding through genetic manipulation a methionine-containing fusion sequence adjacent the EPO molecule. The EPO molecule may then be cleaved from the fused sequence in the presence of cyanogen bromide without destroying the EPO molecule or its activity. This property has several applications in particular for purification and isolation of EPO for both research and clinical therapy.

It is contemplated that the EPO composition of the invention will provide a significant source of EPO for the effective treatment of anemic conditions as well as an important souce for research applications.

What is claimed is:

1. A protein useful in treating anemia having a residue 165 amino acid sequence substantially identical to that of native human erythropoietin and characterized by having leucine at position 54 as measured from the N-terminus.

2. A cDNA encoding the protein of claim 1.

3. A mammalian host cell containing a cDNA of claim 2 said host cell capable of expressing said protein.

4. A therapeutic composition for the treatment of anemia which comprises an effective amount of the protein of claim 1 in admixture with a pharmaceutically acceptable carrier.

* * * * *